United States Patent
Lidman et al.

(10) Patent No.: US 6,829,507 B1
(45) Date of Patent: Dec. 7, 2004

(54) APPARATUS FOR DETERMINING THE ACTUAL STATUS OF A PIEZOELECTRIC SENSOR IN A MEDICAL IMPLANT

(75) Inventors: Johan Lidman, Stockholm (SE); Lars Landelius, Järfälla (SE); Charlotte Kjellman, Stockholm (SE); Kenth Nilsson, Åskersberga (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/787,735
(22) PCT Filed: Sep. 20, 1999
(86) PCT No.: PCT/SE99/01642
§ 371 (c)(1),
(2), (4) Date: Oct. 15, 2001
(87) PCT Pub. No.: WO00/16853
PCT Pub. Date: Mar. 30, 2000

(30) Foreign Application Priority Data

Sep. 21, 1998 (SE) ............................................. 9803197

(51) Int. Cl.$^7$ ................................................. A61N 1/08
(52) U.S. Cl. ......................... 607/19; 600/486; 128/901
(58) Field of Search ............................. 600/508, 509, 600/486; 607/4, 5, 6, 7, 9, 11, 17, 19; 128/901

(56) References Cited

U.S. PATENT DOCUMENTS

| | | | |
|---|---|---|---|
| 5,040,535 A | * 8/1991 | Mann et al. | ................... 607/19 |
| 5,318,596 A | * 6/1994 | Barreras et al. | ............... 607/19 |
| 5,370,667 A | 12/1994 | Alt | |
| 5,472,453 A | 12/1995 | Alt | |
| 5,865,760 A | * 2/1999 | Lidman et al. | .............. 600/509 |

FOREIGN PATENT DOCUMENTS

EP   0 845 240   3/1998

* cited by examiner

Primary Examiner—Jeffrey R. Jastrzab
Assistant Examiner—Frances P. Oropeza
(74) Attorney, Agent, or Firm—Schiff Hardin LLP

(57) ABSTRACT

In an apparatus for determining the actual status of a piezoelectric sensor in a medical implant, electrical charges generated in the sensor, in response to changes in acceleration and/or gravitational force or other loads acting on the sensor, are continuously detected and the charges are then removed from the sensor, thereby maintaining the voltage across the sensor at a substantial constant zero level. The detected charges, both negative and positive, are integrated, thereby providing a resulting integrated signal representing the actual status of the sensor. The integrated signal is then evaluated for determining the physical activity and/or the posture of a patient in whom the medical implant is implanted.

13 Claims, 7 Drawing Sheets

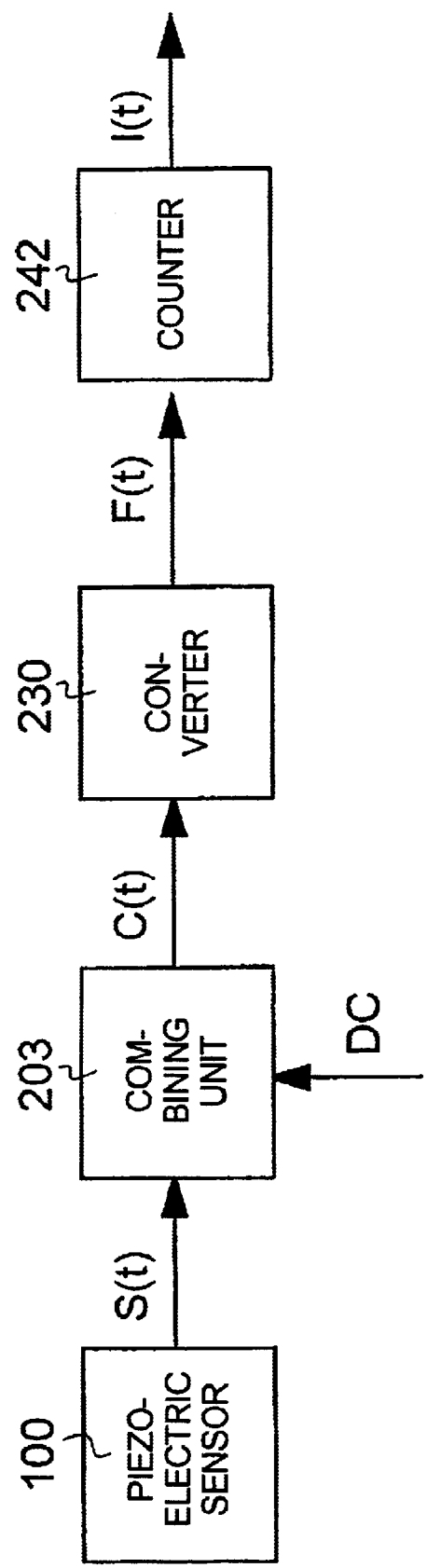

US 6,829,507 B1

APPARATUS FOR DETERMINING THE ACTUAL STATUS OF A PIEZOELECTRIC SENSOR IN A MEDICAL IMPLANT

BACKGROUND OF THE INVENTION

1. Field of the Invention

The present invention relates generally to the field of medical implants. More specifically, the present invention relates to an apparatus for providing a signal representing the status of a sensor in a medical implant.

2. Description of the Prior Art

Ever since the introduction of rate responsive implanted cardiac stimulators, a number of different parameters have been used for determining the activity level of the patient, which in turn is used for controlling the rate at which the heart of a patient is to be stimulated by the pacemaker. One of the most common sensors used is the piezoelectric accelerometer.

Another form of sensor is the intracardiac piezoelectric pressure sensor.

Unlike the piezoresistive and piezocapacitive sensors piezoelectric sensors are not energy consuming, on the contrary they generate their energy themselves. Piezoelectric sensors are also arranged to alter the mechanical stress of the piezoelectric material in response to a change of loads emanating from for instance an acceleration of a seismic mass or from a change in pressure acting on the sensor. This results in a transport of electrons or electrical charges within the material, which provides a change in voltage across the piezoelectric sensor. This voltage corresponds to the load to which the sensor is subjected.

A problem related to measuring the voltage across a piezoelectric sensor is the leakage of charges that occurs, negatively affecting the accuracy of the measurements. In an attempt to solve this problem, use has been made of a voltage amplifier having a very high input impedance. This requires, however, a very large resistance component, which is undesired within a medical implant. Furthermore, the problem related to leaking charges is still not completely eliminated, and the use of a memory function of some sort would be required. The problem of leaking charges is of particular interest when the piezoelectric sensor is subjected to relatively small changes in load over long time periods, such as small changes of pressure over a long time or changes in posture.

SUMMARY OF THE INVENTION

An object of the present invention is to provide a method and apparatus for determining the status of a piezoelectric sensor that takes the leakage of charges mentioned above into account.

A further object of the present invention is to improve the possibilities of evaluating the status of a piezoelectric sensor.

These objects are achieved in accordance with the present invention wherein status related sensor output changes are substantially continuously detected, and based thereupon a signal representing the actual status of a sensor is generated. Advantageously, said signal is generated by integration of the sensor output changes.

Preferably, use is made of a sensor of the type in which status changes generate changes regarding electrical charges in the sensor. Thus, the sensor is suitably of the piezoelectric type.

In accordance with a preferred aspect of the invention, positive and negative charges generated by the sensor, as more closely discussed below, are substantially continuously detected and removed from the sensor, thereby keeping the output voltage of the sensor at a substantially constant zero level, while at the same time providing an output current which can be the basis for an integration in order to produce the signal.

According to an embodiment of the invention, this can be accomplished by connecting the charge-producing sensor to a circuit having the characteristics of an input impedance that is extremely low or redundant. As a result, charges generated by the piezoelectric sensor will immediately leak to, or be collected or removed by, the connected circuit. This also means that there will be no problem with uncontrolled leakage of charges from the sensor, as is the case in the prior art.

As indicated above, a change of load generates a change of charges in a sensor of the piezoelectric type, all charges generated being collected, i.e. detected and removed from the piezoelectric sensor, by the connected circuit. A change of load can be either positive or negative. A positive change of load will generate an internal transport of charges in a direction opposite that caused by a negative change of load. Furthermore, if a transport of charges in one direction generates a positive voltage across the piezoelectric sensor, a transport of charges in the opposite direction generates a negative voltage. Hence, for restoring a zero voltage level across the sensor from a positive voltage level, there must be a transport of "actual" charges from the sensor, while for restoring a zero level from a negative voltage, there must be a transport of "actual" charges from the connected circuit to the sensor.

In accordance with the above, the actual charges supplied to the sensor for restoring a zero level will hereinafter be referred to as collected or removed negative charges, and the resulting current will be referred to as a negative current. Correspondingly, the actual charges removed from the sensor will be referred to as positive charges, and the resulting current as a positive current. Therefore, both the supply and the removal of charges to and from the sensor hereinafter will be referred to as a collection of charges, wherein a supply of charges to the sensor will be referred to as a collection of negative charges, and a removal of charges from the sensor will be referred to as a collection of positive charges.

The charges generated in a sensor of the type discussed correspond to the load (e.g. acceleration and/or gravitational force or pressure) to which the sensor is subjected. Accordingly, each generated charge represents a certain change of load. A greater change of load generates more charges; a more rapid change of load provides a more rapid generation of charges; and an change of load in one direction generates positive charges and an change of load in the opposite direction generates negative charges (in accordance with the above stated definition of positive and negative charges). Hence, the electric charges generated by the sensor per time unit, i.e. electric current, correspond to the amount and the direction of the change of load and, hence, to the time derivative of the load to which the sensor is subjected.

The charges generated by a piezoelectric sensor, as described above, are provided to a circuit for detecting and removing these charges. Since the number of generated charges per time unit, hereinafter referred to as the sensor current or sensor output current, is proportional to the time derivative of the change of load, an integration of said current will result in an integrated value or signal that is proportional to the load.

The circuit for receiving the current (detecting and removing the charges) is, according to the invention, arranged to integrate said current, i.e. to quantify and to cumulate the charges generated by the sensor. Accordingly, the resulting value from this integration will represent the net amount, i.e. considering the sign of the generated charges, of charges generated by the sensor. Thus, the integrated value, or signal, will be directly representative of the load to which the sensor currently is subjected. The integrated value can therefore be seen as a recreation of the voltage that would have existed in the sensor, provided that there would have been no leakage or deliberate removal of charges at all. Thus, the present invention solves the problem regarding obtaining an absolute value representative of the level of for instance a constant acceleration or gravitational force or pressure by the use of a piezoelectric type sensor.

As stated above, the restoring in the sensor of a zero level from a negative voltage level would require a supply of charges from the connected circuit to the sensor. According to an embodiment of the invention, the supply of charges can be provided by connecting a constant direct current, hereinafter referred to as a DC signal, to the sensor and the circuit. If the magnitude of the DC signal exceeds the possible maximum magnitude of the positive and the negative sensor current, the charges or the current supplied to the sensor for restoring the zero level will be provided by the added DC signal. As a result, the connected circuit will be provided with a combined signal, this combined signal being the sum of the DC signal and the sensor current. The combined signal will, e.g., have the magnitude of the DC signal when the sensor is not affected by a change in acceleration and/or gravitational force or pressure; a magnitude greater than the DC signal when the sensor is affected by a positive change in load, for instance acceleration and/or gravitational force; and a magnitude less than the DC signal when the sensor is affected by a negative change in said load.

As described above, the connected circuit integrates the sensor current. According to preferred embodiments of the invention, this integration can be accomplished by first subjecting the sensor current to a current to frequency conversion. The provision of an added DC signal to provide a combined signal, as described above, is particularly advantageous when used in conjunction with a current to frequency converter, in that the combined signal will always be kept positive and the frequency can be kept proportional to the level of the combined signal.

The current to frequency conversion produces a frequency signal that will be provided to a counted means for counting the pulses comprised in the frequency signal. The counting operation will generate the desired integrated value, after compensation for the contribution from the added DC signal, that will be directly representative of the actual acceleration or gravitational force by which the sensor is affected.

The contribution of the added DC signal, however, must be eliminated in order to obtain an integrated signal representing the immediate influence of the load on the sensor. According to an embodiment of the invention, the contribution of the added DC signal can be removed by deducting in the counter a counter value corresponding to the contribution from the DC signal. After each deduction, the counter value, i.e. the integrated value, will represent the contribution from the sensor current only, and, hence, from the load to which the sensor is affected.

The value to be deducted, herein referred to as a deduction value, can be obtained by disconnecting the sensor from the connected circuit for a given time period, and by registering the pulses in the frequency signal during said time period. Disconnection of the sensor can simply be provided by a switch. When this time period expires, the number of pulses registered during this time period is stored as the deduction value and the operation of the connected circuitry continues, using the updated deduction value, as described above. The operation for obtaining the deduction value can be performed at given time intervals, but is preferably performed when there is no sensor current.

In another embodiment of the present invention, the problem in compensating for the contribution of the added DC signal can be solved by providing two parallel signal paths, each path being provided with a separate DC signal, as described above, and including a current to frequency converter, a first switch for switching the sensor current between the two signal paths, a second switch for switching the respective frequency signal from the respective signal path between incrementing and decrementing inputs of an up-down counter, and an up-down counter.

The sensor current is periodically switched between the respective paths, so that the sensor current is half the time provided to the one path, half the time to the other path. As a result, the converted frequency signal output by each path will half the time comprise the converted combined signal, half the time a frequency conversion of the added DC signal. The converted signal, when including the contribution of the DC signal only, can be seen as an idle frequency signal. Obviously, when the sensor current is zero, a frequency conversion of the combined signal will have the same frequency as the idle frequency signal, regardless of the state of the first switch means.

The frequency signal output by each signal path is periodically switched between incrementation and decrementation inputs of an up-down counter. This switching is preferably performed in conjunction with the switching of the sensor current between the respective signal paths, so that the path presently receiving the sensor current is connected to the incrementing input of the up-down counter, and that the path presently not receiving the sensor current is connected to the decrementing input of the up-down counter. Hence, the respective frequency signal will increment the counter when including the contribution of the sensor current, and decrement the counter when not including the contribution of the sensor current. Accordingly, the contribution of the respective added DC signals will be completely eliminated and the integrated value output by the up-down counter will be directly representative of the current generated by the sensor. The contribution of the respective added DC signal will be completely eliminated, regardless of any drift of the DC signal over time and regardless of the difference between the DC signals.

According to this embodiment, the counter value, i.e. the integrated value, is constantly being updated and at all times represents the load to which the sensor presently is subjected.

One way of determining the activity level of a patient is to use a piezoelectric accelerometer in a medical implant to determine the physical activity of the patient and consequently the rate at which the heart of the patient is to be stimulated.

However, the heart rate in a healthy individual is also dependent of the individual's static or long term physical body orientation or posture, or a change from one such orientation to another, e.g. from standing to lying down. The intrinsic heart rate is even dependent of whether the individual is lying in a supine, i.e. on his/her back, or in a prone position, i.e. on his/her face. Therefore, there is a need for establishing both the activity level and the body posture of a pacemaker patient, in order to control the operation of the pacemaker in dependence of the activity level and the posture of the patient.

A number of different methods and devices have been proposed for determining the physical orientation or posture of a patient. Generally, accelerometers are used for determining posture, as described for instance in European Application 0,845,240. This is due to the fact that gravitational force affects an object in the same manner as would a corresponding constant acceleration force. By determining the effect of gravitation on an accelerometer that is sensitive to acceleration forces in a certain direction only, the gravitation component in this direction can be measured and, hence, the angle between the axis of sensitivity and the direction of the gravitational force can be determined. Knowing the orientation of the accelerometer relative the patient, the posture of the patient then can be easily established.

The accelerometer also can be combined with one or more accelerometers having different directions of sensitivity, preferably perpendicular to that of the first accelerometer. Thereby, the possibility of detecting different postures of the patient will increase. For instance, the combination with an accelerometer having a sensitivity in the right-left direction of the patient, would enable distinguishing an upright position from a position where the patient is lying on his/her side.

Since the changes in acceleration and gravity connected with changes in posture are relatively slow compared to the changes in acceleration connected with normal physical activity and the device according to the invention takes the leakage of charges from the piezoelectric accelerometer into account, the invention is of particular interest in piezoelectric devices for detecting changes in posture.

As discussed above, the constantly updated integrated value represents the acceleration and/or gravitational force (i.e. the component of the gravitational force in the direction of sensitivity of the accelerometer) to which the accelerometer presently is subjected. The maximum contribution the accelerometer can be subjected to by the gravitational force corresponds to an acceleration of 1 g (9.81 m/s$^2$). However, accelerations associated with heavy exercise, such as running, can significantly exceed 1 g, sometimes even exceed 2 g. Therefore, the integrated value will suitably be subjected to further processing in order, e.g., to distinguish between contribution from gravitation and contribution from physical activity.

According to an embodiment of the invention, the constantly updated integrated value can be provided as a digital output signal from the described counter to a posture evaluation unit for determining the posture of the patient. This posture evaluation unit, or circuitry connected between the posture evaluation unit and the counter, performs a digital low pass filtering of the integrated signal. This low pass filtering, preferably having a cut-off frequency of less than about 1 Hz, preferably about 0, 5 Hz, will effectively filter out the contributions of activity, heart beats etc. The low pass filtered integrated signal then can be compared to threshold values for obtaining a posture value indicating the actual posture of the patient. This posture value can then be provided to a control unit for controlling the operation of a pacemaker in accordance with the posture of the patient, in a known manner.

Likewise, according to a further embodiment of the invention, the integrated value also can be provided as a digital output signal to an activity evaluation unit for determining the physical activity of the patient. This activity evaluation unit, or circuitry connected between the activity evaluation unit and the counter, performs a digital band pass filtering of the integrated signal. This band pass filtering preferably has a lower cut-off frequency of about 1 Hz, and has a preferred upper cut-off frequency of about 10 Hz, preferably about 6 Hz. The band pass filtered integrated signal can then be evaluated in a known manner for obtaining an activity value indicating the physical activity of the patient. This activity value can then be provided to a control unit for controlling the operation of a pacemaker in accordance with the physical activity and the posture of the patient.

In another embodiment of the invention, use is made of a piezoelectric accelerometer formed by a two layer beam, one piezoelectric layer and one supporting layer, this beam being fixed to a mounting surface at one end and provided with a weight at the other end. Thus, when affected by an acceleration or gravitational force change, the beam will deflect around the fixed end. The beam is preferably wide, which would prevent the beam from twisting or deflecting in other directions than intended. The beam also can be tilted. This tilt and the width of the beam will produce sensitivity to acceleration and gravitation changes in a direction perpendicular to the mounting surface only. Thus, the piezoelectric accelerometer can be said to be of a monoaxial type. The width of the beam also enhances the magnitude of the current generated by the piezoelectric layer. When the accelerometer is subjected to acceleration and/or gravitational forces directed perpendicular to the mounting surface, the beam will deflect around the fixed end, and the piezoelectric material will generate charges in dependence of the rate and magnitude of the acceleration and/or gravitational changes.

Furthermore, according to this embodiment of the invention, the piezoelectric accelerometer is positioned in such a way within a pacemaker that, when the pacemaker is implanted in a patient, the accelerometer beam is positioned vertically with its direction of sensitivity being the anterior-posterior direction of the patient, with the advantages described above. Since the piezoelectric accelerometer is capable of providing negative values, the prone position can easily be distinguished from the supine position.

As indicated above, the invention also is applicable to other piezoelectric sensors, such as endocardial pressure sensors for measuring the intracardiac pressure.

It is for instance possible to determine changes in posture by means of an intracardiac pressure sensor. The hydrostatic pressure acting on the sensor increases when the patient rises from a prone or supine position to an upright position since the vertical distance upwardly from the sensor within the patient that defines the hydrostatic pressure will increase. The effects of an increase in pressure on the pressure sensor will generally be similar to the effects of acceleration or gravity on an accelerometer of the type described above. The arrangement described above used for evaluating the accelerometer signal thus could be used also for evaluating the signal from the pressure sensor. Since a pacer system normally contains some kind of activity sensor, the pressure signal also additionally could be evaluated by means of the signal from the activity sensor in order to better distinguish the rise in pressure resulting from a change in posture from a change in pressure resulting from a change in activity.

A further use of the arrangement according to the invention is to detect long-term changes or drift in the intracardial pressure by means of a pressure sensor.

DESCRIPTION OF THE DRAWINGS

FIG. 5 is a block diagram and FIG. 6 is a circuit diagram of an apparatus according to a second embodiment of the invention.

DESCRIPTION OF THE PREFERRED EMBODIMENTS

Figure 1:
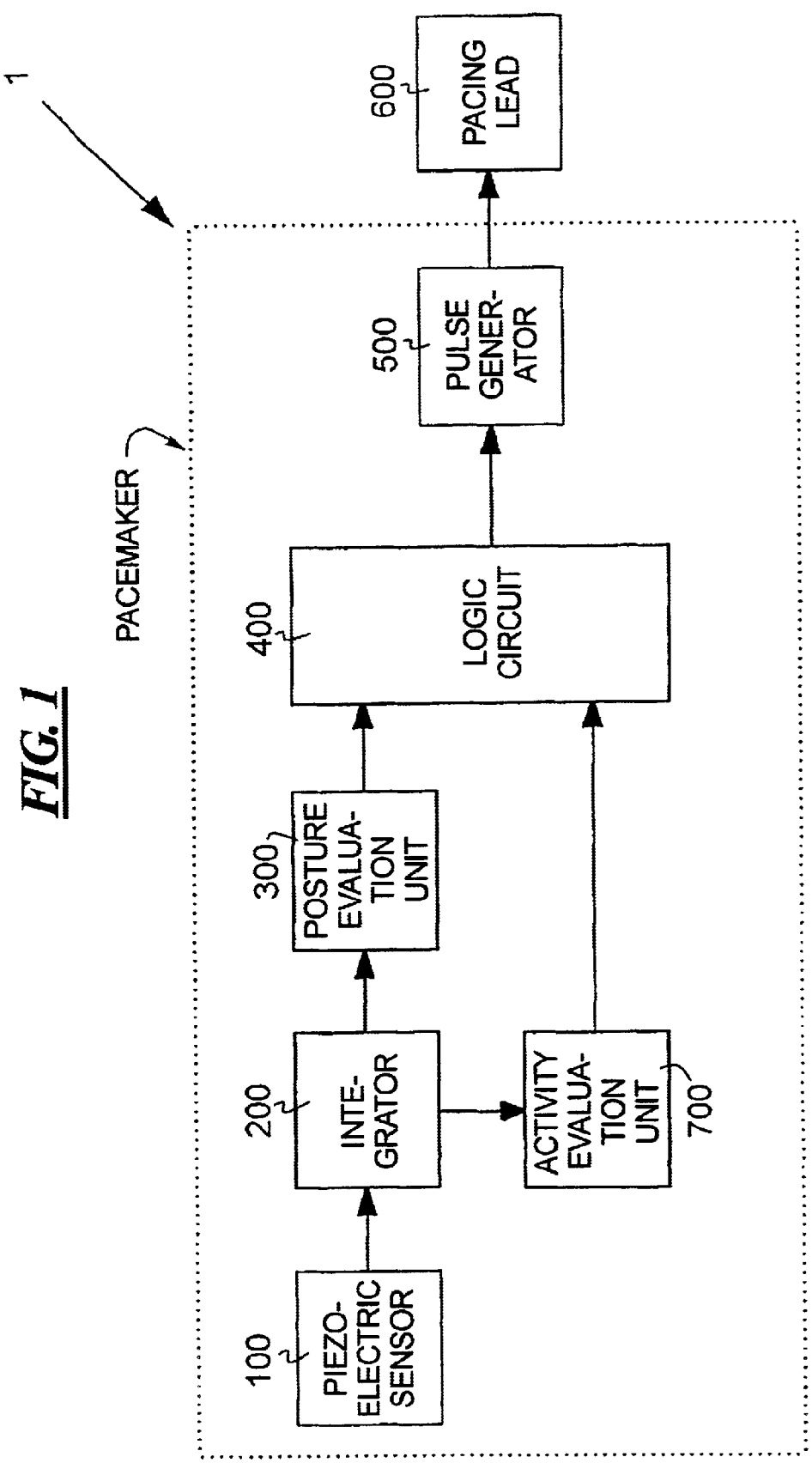
FIG. 1 is a block diagram of a medical implant having an apparatus according to the present invention.

As mentioned above, the invention is applicable to accelerometers and in particular to accelerometers used in connection with pacemakers and similar for detecting changes in posture, and the invention will be described in more detail below with reference to such an accelerometer. Referring to FIG. 1 there is shown a schematic block diagram of a pacemaker 1 according to the invention. The pacemaker 1 according to the invention includes a piezoelectric sensor (accelerometer) 100, an integrator 200, a posture evaluation unit 300, a logic circuit 400, and a pulse generator 500. The logic circuit 400 is also connected to an activity evaluation unit 700, provided with an activity signal originating from the piezoelectric accelerometer 100. The pacemaker 1 is further connected to at least one pacing lead 600 provided with at least one stimulating electrode, this electrode also being used for sensing. The pacemaker 1 further includes processing circuitry for processing the sensing signal(s) from this electrode(s) (not shown). The pacemaker 1 may be arranged for unipolar or bipolar stimulation as is well known to those skilled in the art.

Figure 2:
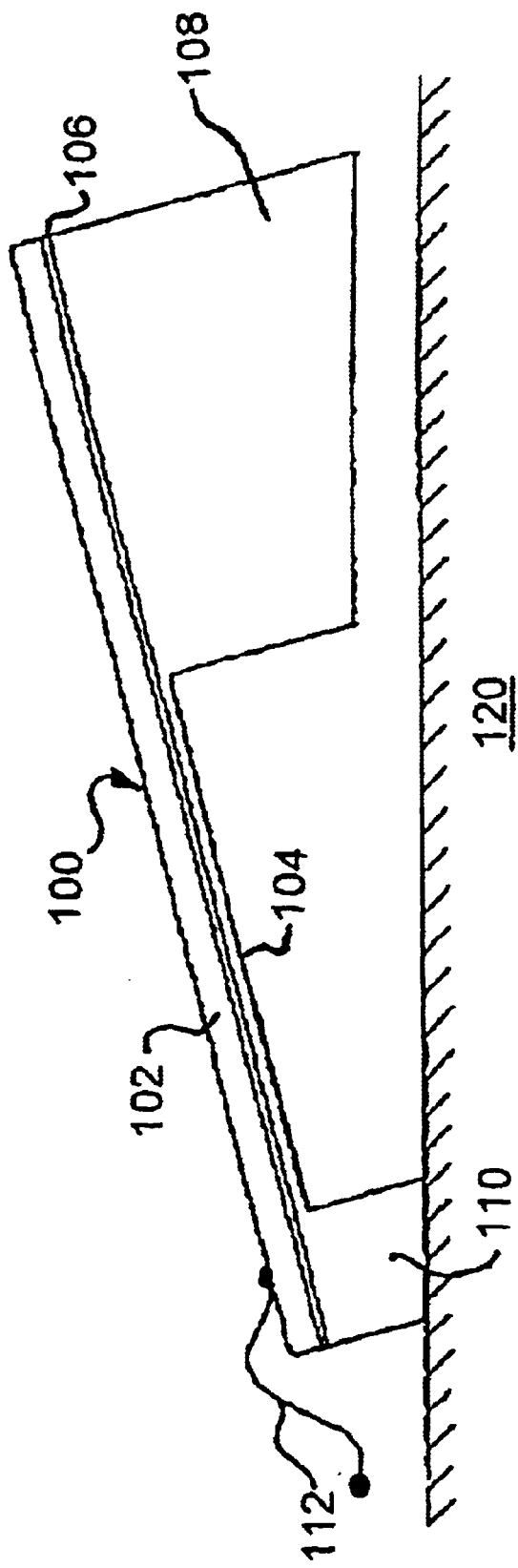
FIG. 2 illustrates a piezoelectric accelerometer according to a preferred embodiment of the present invention.

The piezoelectric accelerometer 100 will now be described with reference to FIG. 2. The pacemaker 1 of FIG. 1 has a piezoelectric monoaxial accelerometer 100, formed by a two layer beam that is at one end fixed via a support 110 to a surface 120, the beam being tilted with respect to the mounting surface 120. The other end, the free end, is provided with a weight (mass) 108 that produces a bending or deflecting motion around the fixed end. The upper layer 102 of the beam is made of a piezoelectric ceramic material, the lower supporting layer 104 is formed of a high density, high Young's module material. The support 110, the weight 108 and the supporting layer 104 are all made in one piece, the piece being electrically conductive. The layers 102, 104 are adhesively fixed to each other using an electrically conductive adhesive 106. The free upper side of the piezoelectric layer is coated with a thin metallic layer serving as an electrode. The piezoelectric layer 102 is connected to surrounding circuitry via the conductive layer 104 and a lead 112, connected to the metallic layer.

Figure 3:
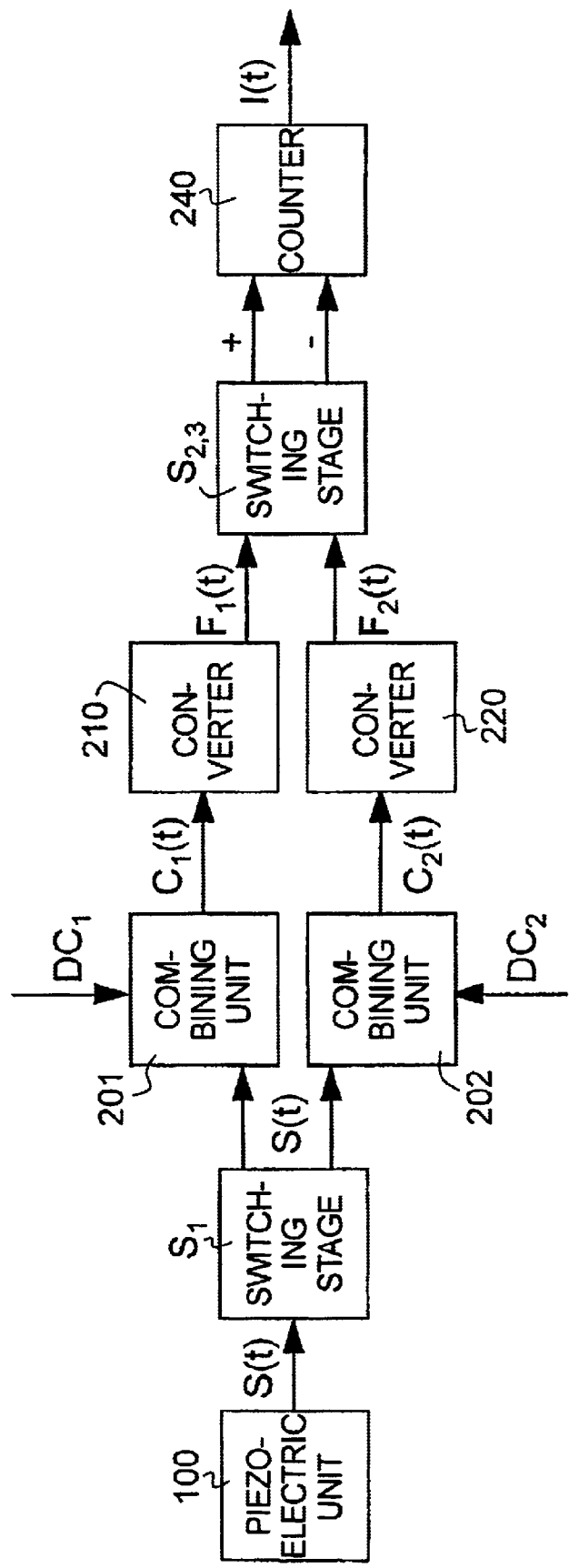
FIG. 3 is a block diagram and FIG. 4 is a circuit diagram of an apparatus according to a first embodiment of the invention.

FIGS. 3 and 5 show the sensor 100 and the integrator 200 according to preferred embodiments of the present invention. The integrator 200 has combining units 201, 202, 203 for combining a sensor output current S(t) with a DC signal, thereby obtaining a combined signal C(t) with an offset DC level; converters 210, 220, 230 for converting the combined signal C(t) into a frequency signal F(t); and counters 240, 242 for subjecting the frequency signal F(t) to a counting operation for obtaining an integrated signal I(t).

Referring specifically to FIG. 3, according to a specific preferred first embodiment of the invention, the integrator 200 further includes a first switch $S_i$, for repeatedly switching the sensor output current S(t) between two parallel signal processing paths, respectively having combining units 201, 202, for combining the sensor output current $5(t)$ with respective DC signals $DC_1$, $DC_2$, thereby obtaining respective combined signals $C_1(t)$, $C_2(t)$, and converters 210, 220, for converting the respective combined signals $C_1(t)$, $C_2(t)$ to respective frequency signals $F_1(t)$, $F_2(t)$. The integrator 200 further has a second switch $S_{2,3}$ for switching the frequency signals $F_1(t)$, $F_2(t)$ between inputs of a counter 240. The counter 240 combines the output signals $F_1(t)$, $F_2(t)$ from the two separate signal processing paths, thereby obtaining the integrated signal I(t).

The apparatus according to the specific first embodiment of the present invention will now be described in greater detail with particular reference to FIGS. 3 and 4. The pacemaker 1 of FIG. 1 has a piezoelectric accelerometer 100, as described above. The integrator 200 of FIG. 1 according to this first embodiment has a first switch $S_1$ for switching the output signal S(t) from the piezoelectric accelerometer 100 between two parallel, substantially similar signal paths. The switch $S_1$ is controlled by a constant, periodic control signal that ensures that the output signal S(t) from the sensor is provided equal time to the respective signal paths. The switching frequency is typically set from about 100 to about 1000 Hz.

The integrator 200, in each of the signal paths, also includes counters 201, 202, for combining the output current $3(t)$ from the piezoelectric accelerometer 100 with a DC signal originating from current sources $DC_1$, $DC_2$, thereby providing combined signals $C_1(t)$, $C_2(t)$. The magnitude of the added DC signals $DC_1$, $DC_2$ is greater than the expected maximum value of the accelerometer current from the piezoelectric accelerometer 100.

When the switch $S_1$ is in a position for switching the sensor output current S(t) to one signal path, the output from the combining units 201, 202 in the respective other signal paths includes only the respective added DC signal.

Furthermore, each signal path of the integrator 200 includes a converter 210, 220, in the form of an amplifier circuit functioning as a current to frequency converter, for converting the respective combined signals $C_1(t)$, $C_2(t)$ into respective frequency signals $F_1(t)$, $F_2(t)$. The amplifier circuits respectively include first operational amplifiers (op amp) 212, 222; first and second capacitors 214, 216, 224, 226, four switches $S_{11}$–$S_{14}$, $S_{21}$–$S_{24}$; and comparators 218, 228. The respective combined signals $C_1(t)$, $C_2(t)$, with or without the contribution of the sensor output current $5(t)$, are provided to the first operational amplifiers 212, 222.

Figure 4:
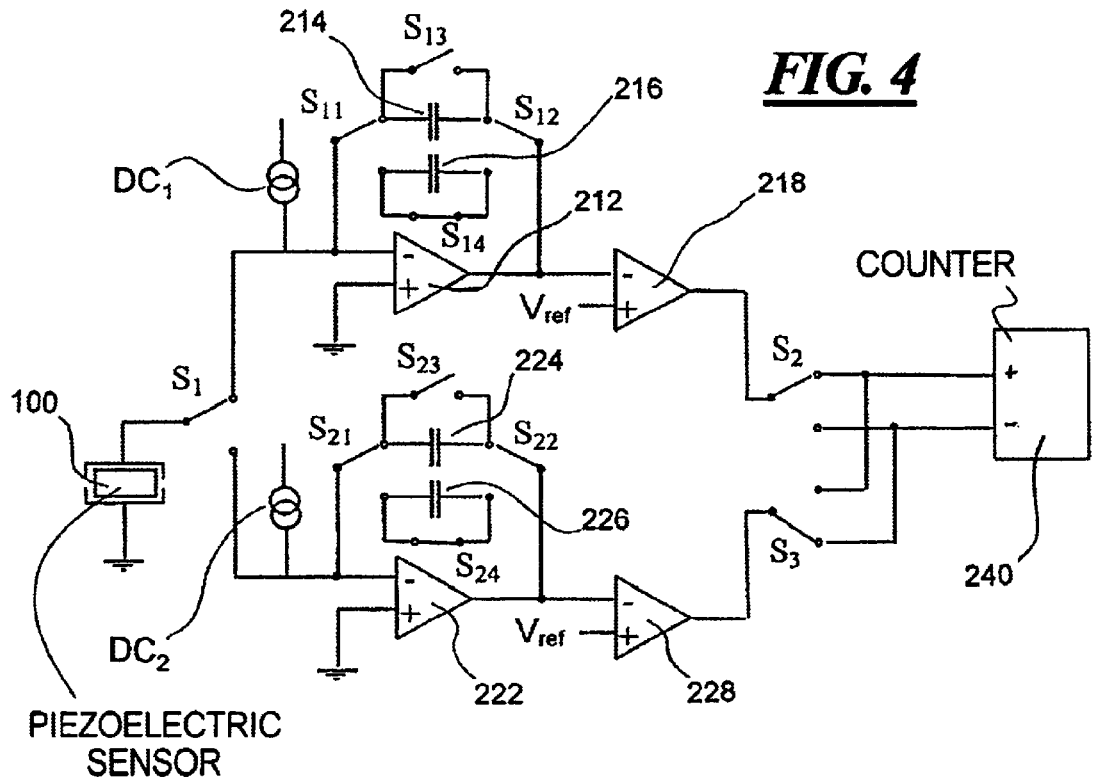

When the switches $S_{11}$–$S_{14}$, $S_{21}$–$S_{24}$ are in the states shown in FIG. 4, the first operational amplifiers 212, 222 are respectively fed back by the first capacitors 214, 224 and charge the respective capacitors 214, 224. The comparators 218, 228, each shown as a second operational amplifier, respectively compare the charge of the first capacitors 214, 224 to a reference voltage $V_{ref}$.

When the charge of either of the first capacitors 214, 224 exceeds the reference voltage, the respectively connected comparators 218, 228 provides an output signal that produces switching of the switches $S_{11}$–$S_{14}$ or $S_{21}$–$S_{24}$ to their second state, thereby discharging the first capacitor 214 or 224 and charging of the second capacitor 216 or 226 commences. When the input signal to either comparator 218, 228 once again exceeds the reference voltage $V_{ref}$, the switches $S_{11-14}$ or $S_{21}$–$S_{24}$ switch back again and the procedure is repeated. The respective output signals of the comparators 218, 228 represent the frequency with which the first and second capacitors 214, 216, 224, 226 are discharged. Thus, the respective outputs from the comparators 218, 228 provide respective frequency signals $F_1(t)$, $F_2(t)$.

The rate at which the capacitors are discharged obviously depends of the current level of the combined input signal $C_1(t)$ or $C_2(t)$. However, the level of the combined signal $C_1(t)$ or $C_2(t)$ is selected so that the frequency of the output frequency signal $F_1(t)$ or $F_2(t)$, converted from the combined signal $C_1(t)$ or $C_2(t)$, always exceeds the switching frequency for switching the switch $S_1$. Actually, half the time, the combined signal will be composed solely of the DC signal $DC_1$ or $DC_2$. When the signal path receives the combined signal $C_1(t)$ or $C_2(t)$ solely containing the DC signal contribution, the output from the comparator 218 or 228 constitutes an idle frequency signal $F_{O1}$ or $F_{O2}$. The frequency of said idle frequency signal $F_{O1}$ or $F_{O2}$ will be in the magnitude of 10–100 kHz, i.e. by far exceeding the switching frequency for switching the switch S1.

The integrator 200 further has a switching stage $S_{2,3}$ in the form of a first switch $S_2$ and a second switch $S_3$, for respectively switching the output frequency signals $F_1(t)$, $F_2(t)$ from the respective signal paths between the respective positive and negative inputs of a counter 240. The first and second switches $S_2$, $S_3$ operate in an opposed manner so that when the first switch $S_2$ connects one signal path to the positive input of the counter 240, the second switch $S_3$ connects the other signal path to the negative input of the counter 240. The switches 32, 33 are controlled by the same constant, periodic control signal noted above with respect to controlling the switch $S_1$, this switching frequency being 20 Hz. Thus, the respective signal paths are connected to one input of the counter 240, i.e. the positive input, when the path is currently receiving the sensor output current S(t), and, accordingly, are connected to the other input, i.e. the negative input, when the path is not receiving the output signal S(t) from the piezoelectric accelerometer 100.

The integrator 200 further has a counter 240 in the form of an up-down counter for counting the pulses of the frequency signals $F_1(t)$, $F_2(t)$ produced by the above described comparators 218 and 228, thereby obtaining the integrated signal I(t). The up-down counter 240 includes a positive input for incrementing the counter 240 and a negative input for decrementing the counter 240. Each output pulse included in the frequency signal $F_1(t)$ or $F_2(t)$ emitted by the respective comparators 219, 229 produces an incrementation or a decrementation of the counter 240, depending of the state of the switches $S_2$ and $S_3$.

The pacemaker 1 shown in FIG. 1 further has a posture evaluation unit 300 for evaluating the integrated signal I(t) and obtaining a value directly representative of the physical posture of the patient. The digital low pass filtering with a cut-off frequency of 0, 5 Hz is performed by the posture evaluation unit 300, or by means not shown connected between the integrator 200 and the evaluation unit 300. The posture evaluation unit 300 further compares, at certain predetermined time intervals, the integrated, digitally low pass filtered signal to predefined threshold values. The evaluation unit 300 provides a signal to the logic circuit 400 indicative of the following physical posture states when the accelerometer 100 is subjected to a gravitational force contribution corresponding to an acceleration of:

1 g, patient lying in a prone position;

0 g, patient being in an upright position; and

−1 g, patient lying in a supine position.

The evaluation unit 300 can also provide a signal indicative of uncertain posture, e.g. when the posture of the patient changes from a supine to standing position.

According to a specific embodiment of the invention, the pacemaker 1 also has an activity evaluation unit 700 for providing a signal to the logic circuit 400 indicative of the current patient activity. In accordance with the posture evaluation unit 300, the integrated signal I(t) is subjected to a digital band pass filtering for removing signal contribution that is not related to patient physical activity. The upper and lower cut-off frequencies of the digital band pass filtering are 1 Hz and 6 Hz, respectively. The digital band pass filtering per se can be performed in a manner well known to those skilled in the art, and will therefore not be described in greater detail. The output signal from the activity evaluation unit 700 is then provided to the logic circuit 400.

The pacemaker 1 shown in FIG. 1 further has a logic circuit 400 and a pulse generator 500 for controlling, regulating and delivering pacing pulses, via the pacing leads, to the atrium and/or ventricle of the heart. This control is performed at least on the basis of the posture and activity of the patient in a manner known to those skilled in the art. It should be understood that means and circuits required for the conventional operation of a pacemaker according to the state of the art are included in the pacemaker according to the present invention, although not shown or described here in.

Figure 7:
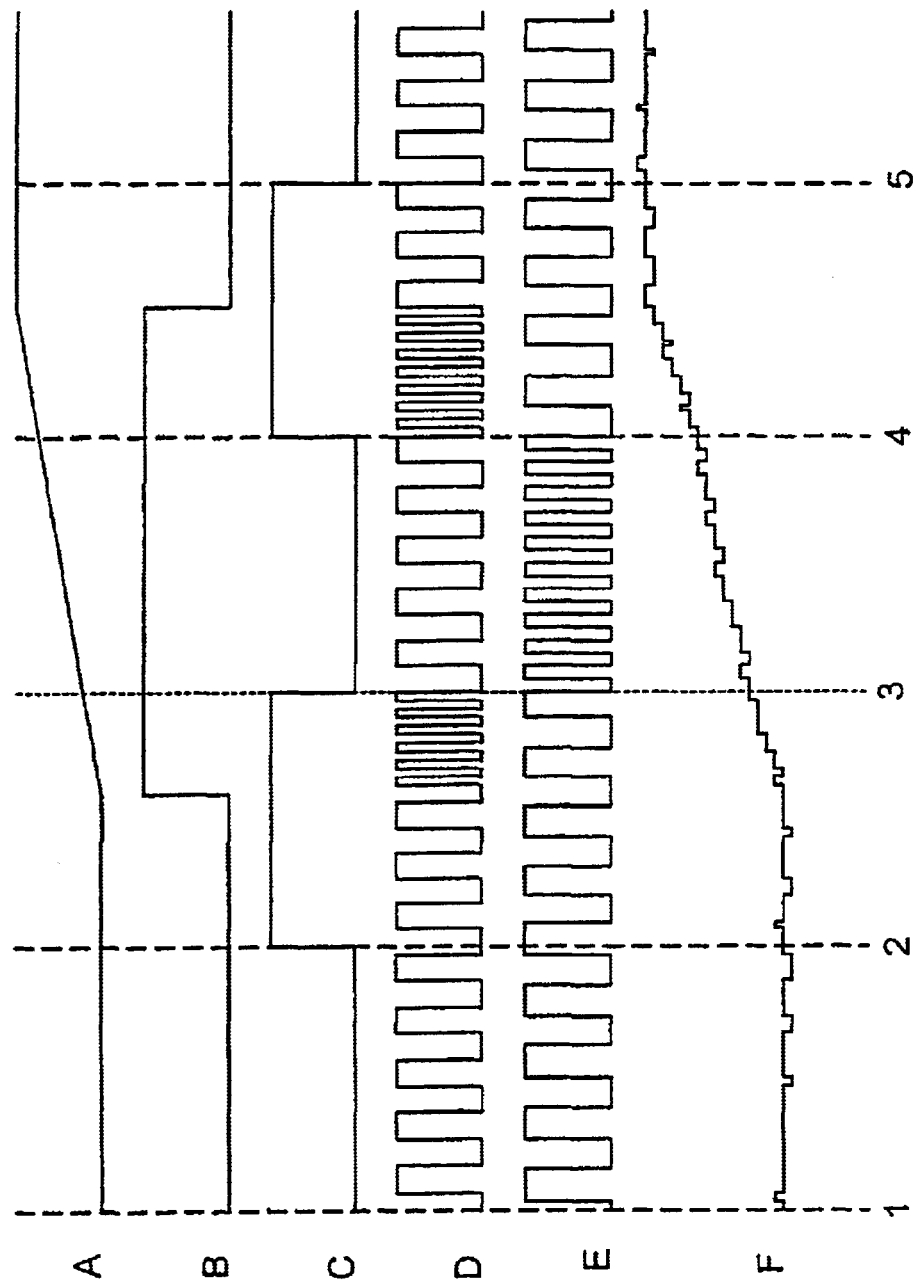
FIG. 7 is a pulse diagram illustrating the method according to the present invention.

FIG. 7 shows in diagrammatic form how an acceleration contribution, in an idealized form for explanatory reasons, is represented by the integrated signal. The pulse diagram has six different signals (A–F) divided into five time periods by the dotted lines (1–5).

A is the idealised contribution of the gravitation component, in the sensitivity direction of the accelerometer, to which the accelerometer is affected. In a true case, this would be superimposed by the activity and noise contributions constantly present.

B is the current generated by a piezoelectric accelerometer that is subjected to the gravitation component according to A, i.e. the sensor output current S(t). This current is proportional to the derivative of the acceleration.

C is the control signal controlling the switches $S_1$–$S_3$, i.e. the switching of the sensor output current S(t) between the parallel signal paths and the switching to the up-down counter 240.

D are the output signal pulses delivered by the comparator 218 of the upper signal path, and E are the pulses delivered by the comparator 228 of the lower signal path, in the manner described above. The respective pulses control the respective switches $S_{11}$–$S_{24}$ and trigger the incrementation and decrementation of the up-down counter 240. The difference in pulse width is only to illustrate the fact that a difference in the magnitude of the respective DC signals $DC_1$ and $DC_2$ does not affect the performance of the integrator 200. The contributions of the DC signals $DC_1$ and $DC_2$ are completely eliminated.

F is the resulting integrated signal I(t) registered in the counter 240 and provided to the posture evaluation unit 300.

During the time intervals 1–2, 3–4 and 5–6, the sensor output current S(t) is switched to the upper signal path, the comparator of which is switched to the positive input of the up-down counter 240. Accordingly, during these time intervals, signal D increments and signal E decrements the up-down counter 240. Consequently, during time periods 2–3 and 4–5, the sensor output current is switched to the lower signal path L, signal E increments the counter and signal D decrements the counter.

As can be seen in FIG. 7, the level of the integrated signal I(t) provided by the counter 240 closely matches the gravitation component to which the piezoelec-tric accelerometer 100 currently is subjected. Hence, the output of the integrator 200 according to the invention provides a direct absolute value representing the current deflection of the accelerometer beam and, hence, the current gravitation (or acceleration)

Figure 6:
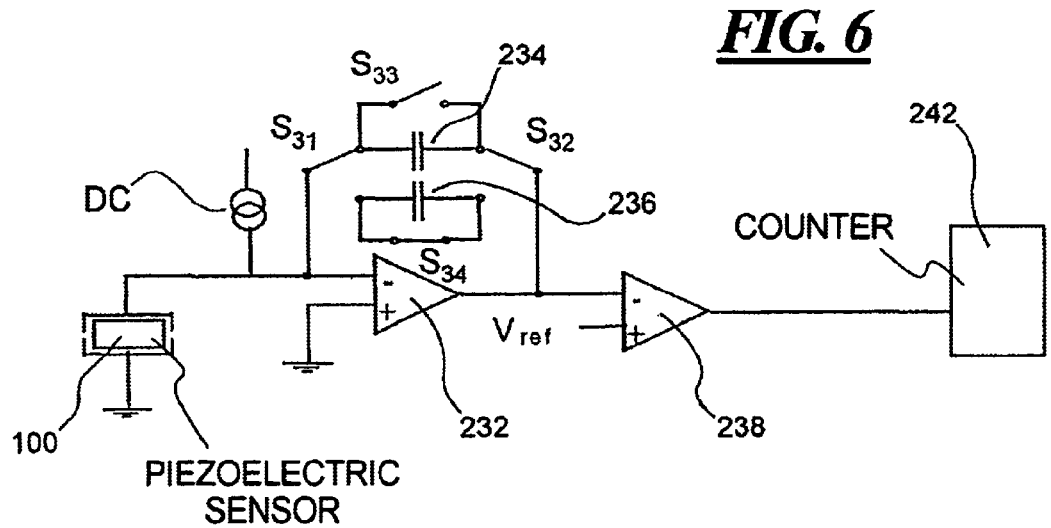

Now, with particular reference to FIGS. 5 and 6, an apparatus according to an alternative second embodiment of the invention will be described. According to this alternative second embodiment, the integrator 200 shown in FIG. 1 has only one signal path, thereby precluding the need for first and second switching stages for switching the sensor output current S(t) between separate signal paths. As noted above, the integrator 200 has a combining unit 203, a converter 230, and a counter 242. The converter 230 is in the form of an amplifier circuit. This amplifier circuit has a first operational amplifier 232, first and second capacitors 234, 236, four switches $S_{31}$–$S_{34}$ and a comparator 238. The functions of the combining unit 203, the converter 230, and the components in the converter 230, are similar to the functions of the corresponding components described above with particular reference to the FIGS. 3 and 4, and therefore need not be described again in detail.

The counter 242, according to this second embodiment, is a counter for counting the pulses of the frequency signal F(t), produced by the comparator 238. As described above, the DC signal is superimposed on the sensor output current S(t). The contribution from the DC signal is removed by deducting, at predefined time intervals, e.g. every 1–10 ms, a counter value corresponding to the contribution from the DC signal. The integrated signal I(t) from the counter is updated after each deduction, and the integrated signal I(t) is representative of the acceleration or gravitation.

The counter value to be deducted, a deduction value, is obtained by disconnecting, at certain given time intervals, e.g. 1 hour, for a given time period, e.g. 1 sec, the piezoelectric accelerometer 100 from the combining unit 203 by the opening of a switch (not shown) positioned between the accelerometer 100 and the combining unit 203. When the time period expires, the number of pulses registered during this time period is stored as the new deduction value, the switch is closed, and the operation of the integrator 200 continues, with the updated deduction value, as described above.

The pacemaker 1, according to this second embodiment of the invention, also has a posture evaluation unit 300, a logic circuit 400, a pulse generator 500, and an activity evaluation unit 700, in the same manner and with the same functions as described above with reference to the first embodiment of the invention.

In a third embodiment the posture may be evaluated with an intracardiac pressure sensor. The hydrostatic pressure acting on the sensor increases when the patient rises from a prone or supine position to an upright position since the vertical distance upwardly from the sensor within the patient that defines the hydrostatic pressure will increase. The effects of an increase in pressure on the pressure sensor will generally be similar to the effects of acceleration or gravity on an accelerometer of the type described above. The arrangement described above used for evaluating the accelerometer signal thus could be used also for evaluating the signal from the pressure sensor. Since a pacer system normally contains some kind of activity sensor, the pressure signal also additionally could be evaluated by means of the signal from the activity sensor in order to better distinguish the rise in pressure resulting from a change in posture from a change in pressure resulting from a change in activity.

Figure 8:
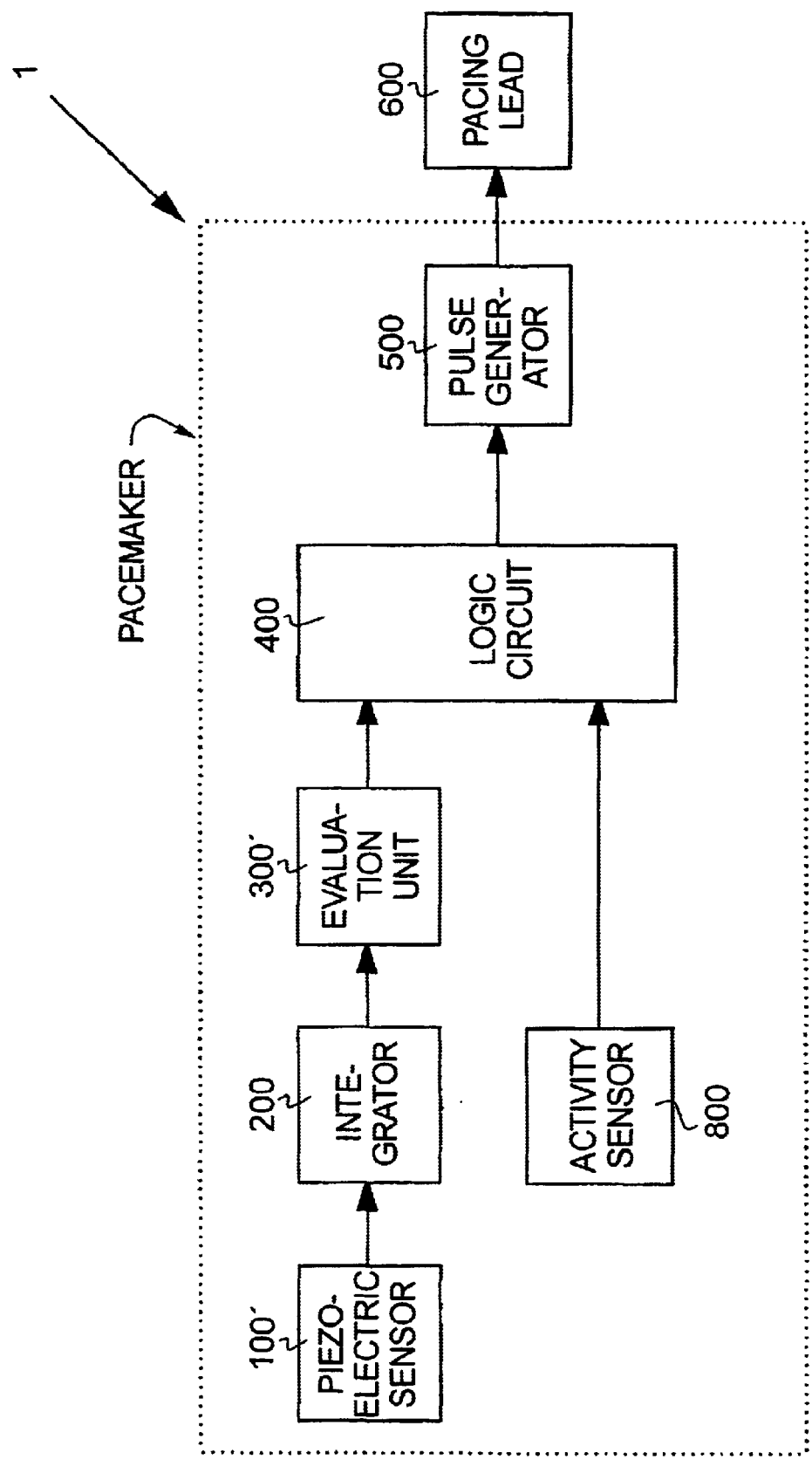
FIG. 8 is a block diagram of an apparatus according to a third embodiment of the invention.

FIG. 8 shows a schematic block diagram of a pacemaker 1 according to the invention including a piezoelectric sensor (pressure sensor) 100', integrator 200, a posture evaluation unit 300', a logic circuit 400, and a pulse generator 500. The logic circuit 400 is also connected to an activity sensor 800. The features in FIG. 8 that are identical to features in FIG. 1 have the same reference numerals as in FIG. 1. The pacemaker 1 is further connected to at least one pacing lead 600 provided with at least one stimulating electrode, this electrode also being used for sensing. The pacemaker 1 further includes processing circuitry for processing the sensing signal(s) from the electrode(s) (not shown). The pacemaker 1 may be arranged for unipolar or bipolar stimulation in a fashion that is well known to those skilled in the art.

The pacemaker 1 shown in FIG. 8 thus also comprises a posture evaluation unit 300' for evaluating the integrated signal I(t) and obtaining a value directly representative of the physical posture of the patient. The digital low pass filtering with a cut-off frequency of 0.5 Hz is performed by the posture evaluation unit 300', or by means not shown connected between the integration unit 200 and the evaluation unit 300'. The posture evaluation unit 300' further compares, at certain predetermined time intervals, the integrated, digitally low pass filtered signal to predefined threshold values. The evaluation unit 300' provides a signal to the logic circuit 400 indicative of different physical posture states, e.g. an increase of about 20 mm Hg would indicate an upright position. Although it may be conceivable to evaluate the physical activity of the patient by means of the short-term characteristics of the pressure signal per se in order to better distinguish the rise in pressure resulting from a change in posture from a change in pressure resulting from a change in activity, it is preferred that the pressure signal also additionally is evaluated by means of the signal from a separate activity sensor, such as the activity sensor 800. Separate activity sensors are standard features in pacers. It should be noted that in the above embodiment relating to an accelerometer, this accelerometer primarily is an activity sensor and therefore there is no need of a further sensor to check whether a signal indicating a change of posture is a result of a sudden activity or not.

In similarity to the accelerometer-based activity signal used in the two first embodiments described above for determining the posture, the pressure signal also contains components that vary comparatively rapidly with the heart beats. These components would correspond to the constantly present activity and noise contributions superimposed on signal A in FIG. 7 and would be superimposed on a pressure signal reflecting the hydrostatic pressure that in turn corresponds to the signal A in FIG. 7.

The design of the circuits otherwise is identical to the circuits used above in connection with the above embodiments for an accelerometer.

The intracardiac pressure may, however, also have a component that varies slowly over relatively long time periods, resulting in a very low variation per time unit. These long-term variations also can be detected by means of the above third embodiment of the invention. This is also indicated in FIG. 8 with the reference numeral 300" denoting an analyzer for a long-term trend of change of pressure. This analyzer 300" is, however, in principle identical to the posture detecting units 300 and 300', the main difference being that the low-pass filter in the trend analysis analyzer 300" has a cut-off frequency that is considerably lower than the cut-off frequency in the filters in the evaluation unit 300 and 300' and may for instance be 0.05 Hz.

Although modifications and changes may be suggested by those skilled in the art, it is the intention of the inventors to embody within the patent warranted hereon all changes and modifications as reasonably and properly come within the scope of their contribution to the art.

What is claimed is:

1. An apparatus for providing a signal representing a status of a sensor in a medical implant, comprising:
    a sensor which generates positive and negative charges respectively in response to positive and negative changes in a load, selected from the group consisting of acceleration forces, gravitational forces and pressure, acting on said sensor;
    a circuit for detecting all positive and negative charges generated by said sensor and, after detecting said charges, for removing substantially all of said generated positive and negative charges from said sensor, for maintaining an accumulated charge potential of said sensor at a substantially zero level, and for generating a sensor output current from said detected positive and negative charges;
    an integrator supplied with said sensor output current which integrates said sensor output current to produce an integrated signal representing a status of said sensor; and
    said integrator including a current-to-frequency converter which converts said sensor output current into a frequency signal having a frequency representing a level of said sensor output current, and a counter supplied with said frequency signal for subjecting said frequency signal to a counting operation to obtain said integrated signal.

2. An apparatus as claimed in claim 1 wherein said sensor is a piezoelectric sensor.

3. An apparatus as claimed in claim 1 wherein said integrator further includes:
    a combining unit for combining said sensor output signal with a DC signal, to obtain a combined signal having an offset DC level, said DC signal being such that a change of sign of said sensor output current does not result in any change of sign of said combined signal, said combine signal being supplied to said current-to-frequency converter, and causing an output from said counter to contain an integration contribution from said DC signal; and
    a unit supplied with said output from said counter for removing said integration contribution from said DC signal to produce said integrated signal.

4. An apparatus as claimed in claim 3 wherein said unit for removing said integrated contribution from said DC signal comprises:
    a first switching stage for repeatedly switching said sensor output current between two parallel signal processing paths;
    in each of said two parallel signal processing paths, a unit for generating a processing path output signal which comprises an information output signal dependent on said combined signal when the signal processing path containing the unit is receiving the sensor output current and which comprises an idle output signal dependent on said DC signal when the signal processing path containing the unit is not receiving the sensor output current; and
    a unit which combines the respective output signals from said two parallel signal processing paths.

5. An apparatus as claimed in claim 4 wherein each of said two parallel signal processing paths comprises:
    a signal path combiner for combining the sensor output current, when said sensor output current is received in the signal processing path, with said DC signal to obtain a signal path combined signal having said DC offset level; and
    a converter for combining the signal path combined signal into a frequency signal having a frequency corresponding to a level of the frequency path combined signal, so that said output signal has a non-zero frequency; and
wherein said unit for combining said output signals from the two parallel signal processing paths is a counter.

6. An apparatus as claimed in claim 3 wherein said integrator further includes:
    a first capacitor and a second capacitor;
    circuitry supplied with said combined signal for alternatingly charging and discharging said first and second capacitors dependent on said combined signal so that when one of said first and second capacitors as being charged by said combined signal the other of said first and second capacitors is being discharged, said circuitry causing a completed charging of said first capacitor to initiate discharging of said first capacitor and charging of said second capacitor, and vice versa, and wherein each discharging of each of said first and second capacitors generates a discharge pulse, thereby producing a plurality of discharge pulses; and
    a counter supplied with said discharged pulses for counting said discharge pulses and thereby generating a count value representing an integrated signal of said combined signal.

7. An apparatus as claimed in claim 6 wherein said counter includes circuitry for removing an integration contribution from said DC signal by deducting from said count value a deduction value corresponding to said integration contribution, thereby generating a reduced count value forming said integrated signal.

8. An apparatus as claimed in claim 1 further comprising an evaluation unit supplied with said integrated signal for evaluating said integrated signal to obtain information relating to said status of said sensor, said evaluating unit including a filter for filtering out unwanted information from said integrated signal.

9. An apparatus as claimed in claim 8 wherein said filter subjects said integrated signal to low-pass filtering to obtain a low-pass filtered signal, and wherein said evaluating unit includes a unit for evaluating said low-pass filtered signal to generate a value representing an orientation of said medical implant.

10. An apparatus as claimed in claim 9 wherein said unit for evaluating said low-pass filtered signal compares said low-pass filtered signal to respective, predetermined threshold values, said threshold values respectively corresponding to predetermined orientations of said medical implant, to obtain a comparison result as said value representing an orientation of the medical implant.

11. An apparatus as claimed in claim 8 further comprising an additional evaluating unit containing a bandpass filter for bandpass filtering said integrated signal to obtain a bandpass filtered signal, and a unit for evaluating said bandpass filtered signal to obtain a value representing a physical activity level of a person in whom said medical implant is implanted.

12. An apparatus as claimed in claim 1 wherein said sensor is sensitive to positive and negative changes in said load in only one direction.

13. An apparatus as claimed in claim 1 wherein said sensor is a piezoelectric sensor, and further comprising an activity sensing unit supplied with said sensor signal which identifies whether said changes in said load on said piezoelectric sensor result from physical activity of a patient in whom said medical implant is implanted.

* * * * *